(12) United States Patent
Hayashi et al.

(10) Patent No.: US 11,872,147 B2
(45) Date of Patent: Jan. 16, 2024

(54) STENT

(71) Applicant: OLYMPUS CORPORATION, Tokyo (JP)

(72) Inventors: Toshiaki Hayashi, Tokyo (JP); Kazuhiro Kan, Tokyo (JP); Masao Akai, Tokyo (JP); Kenji Murakami, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 239 days.

(21) Appl. No.: 17/190,884

(22) Filed: Mar. 3, 2021

(65) Prior Publication Data
US 2021/0186724 A1 Jun. 24, 2021

Related U.S. Application Data

(63) Continuation of application No. PCT/JP2019/034701, filed on Sep. 4, 2019.

(30) Foreign Application Priority Data

Sep. 7, 2018 (WO) .................. PCT/JP2018/033291

(51) Int. Cl.
*A61F 2/915* (2013.01)
*A61F 2/82* (2013.01)
*A61F 2/86* (2013.01)

(52) U.S. Cl.
CPC ............... *A61F 2/915* (2013.01); *A61F 2/82* (2013.01); *A61F 2/86* (2013.01); *A61F 2002/91575* (2013.01)

(58) Field of Classification Search
CPC ...... A61F 2/07; A61F 2/82; A61F 2/86; A61F 2/915; A61F 2002/91575; A61F 2220/0075
See application file for complete search history.

(56) References Cited

U.S. PATENT DOCUMENTS 6,241,757 B1 * 6/2001 An .................. D04G 1/06
623/1.1
2003/0114922 A1 6/2003 Iwasaka et al.
(Continued)

FOREIGN PATENT DOCUMENTS

JP H08-509899 A 10/1996
JP 2003-510162 A 3/2003
(Continued)

OTHER PUBLICATIONS

JP 2004-049804 with English translation (Year: 2004).*
(Continued)

*Primary Examiner* — Dinah Baria
(74) *Attorney, Agent, or Firm* — Scully, Scott, Murphy & Presser, P.C.

(57) ABSTRACT

A stent includes a first tubular unit that has a cylindrical tubular shape and a mesh circumferential surface; and a second tubular unit that has a cylindrical tubular shape and a mesh circumferential surface, and is connected to the first tubular unit in a longitudinal axis direction of the stent. The first tubular unit has a first-first direction bent portion which is bent to be convex toward the first direction side that is one side of the longitudinal axis direction, the second tubular unit has a second-second direction bent portion which is bent to be convex toward the second direction side that is the other side of the longitudinal axis direction, and the first-first direction bent portion and the second-second direction bent portion form a first connecting portion that is connected so as to be relatively movable.

17 Claims, 14 Drawing Sheets

(56) References Cited

U.S. PATENT DOCUMENTS

2005/0125051 A1    6/2005   Eidenschink et al.
2013/0226282 A1    8/2013   Ahn et al.

FOREIGN PATENT DOCUMENTS

| JP | 2003-135064 A | 5/2003 |
| JP | 2004-049804 A | 2/2004 |
| JP | 2004-528862 A | 9/2004 |
| JP | 2005-110779 A | 4/2005 |
| JP | 3708923 B2 | 10/2005 |
| WO | WO 95/26695 A2 | 10/1995 |
| WO | WO 01/24735 A1 | 4/2001 |

OTHER PUBLICATIONS

International Search Report dated Nov. 26, 2019 issued in PCT/JP2019/034701.
International Search Report dated Oct. 16, 2018 issued in PCT/JP2018/033291.

* cited by examiner

STENT

The present invention relates to a stent. Priority is claimed on PCT/JP2018/033291, filed Sep. 7, 2018, and PCT/JP2019/034701, filed on Sep. 4, 2019, the contents of which are incorporated herein by reference.

BACKGROUND

In recent years, stent placement has been used to expand and hold a lumen of a tubular organ by placing a stent made of a wire rod (wire) or the like in a diseased part in which a stenosis or occlusion has occurred in the lumen of the tubular organ in the living body.

A stent having self-expandability (self-expandable stent) is delivered by a delivery system to a diseased part in which a stenosis or occlusion has occurred in a reduced diameter state. The stent released from the delivery system expands in diameter by self-expandability to expand the stenosis and occlusion.

In many cases, the lumen in which such a stent is placed is bent, and thus the stent needs to have a function of maintaining the shape corresponding to the shape of the bent lumen (pipeline shape-maintaining function). In a case where the stent having the pipeline shape-maintaining function is placed in a bent lumen, the stent can maintain a shape corresponding to the shape of the bent lumen without returning to the original shape of the stent due to reaction force.

The expansion mechanism using the shape memory alloy disclosed in Japanese Patent No. 3708923 can expand the stenosis part of the body. The expansion mechanism disclosed in Japanese Patent No. 3708923 has a "meshing portion" that is extendible and contractible in the axial direction, and can maintain the shape corresponding to the shape of the lumen regardless of the lumen shape of the stenosis part.

SUMMARY

A first aspect relates to a stent that expands a lumen of a living body, the stent including a first tubular unit that has a cylindrical tubular shape and a mesh circumferential surface; and a second tubular unit that has a cylindrical tubular shape and a mesh circumferential surface, and is connected to the first tubular unit in a longitudinal axis direction of the stent. The first tubular unit has a first-first direction bent portion which is bent to be convex toward the first direction side that is one side of the longitudinal axis direction, the second tubular unit has a second-second direction bent portion which is bent to be convex toward the second direction side that is the other side of the longitudinal axis direction, and the first-first direction bent portion and the second-second direction bent portion form a first connecting portion that is connected so as to be relatively movable.

A second aspect relates to a stent including a first region having a cylindrical tubular shape; a second region that has a cylindrical tubular shape and is connected to the first region in a longitudinal axis direction of the stent; a first-first direction bending portion provided at the first region and which is bent to be convex toward the first direction side that is one side of the longitudinal axis direction; a second-second direction bending portion provided at the second region and which is bent to be convex toward the second direction side that is the other side of the longitudinal axis direction; and a first connecting portion configured to be formed by connecting the first-first direction bending portion and the second-second direction bending portion so as to be relatively movable.

DETAILED DESCRIPTION OF THE PREFERRED EMBODIMENTS

First Embodiment

A first embodiment will be described with reference to FIGS. 1 to 7.

Figure 1:
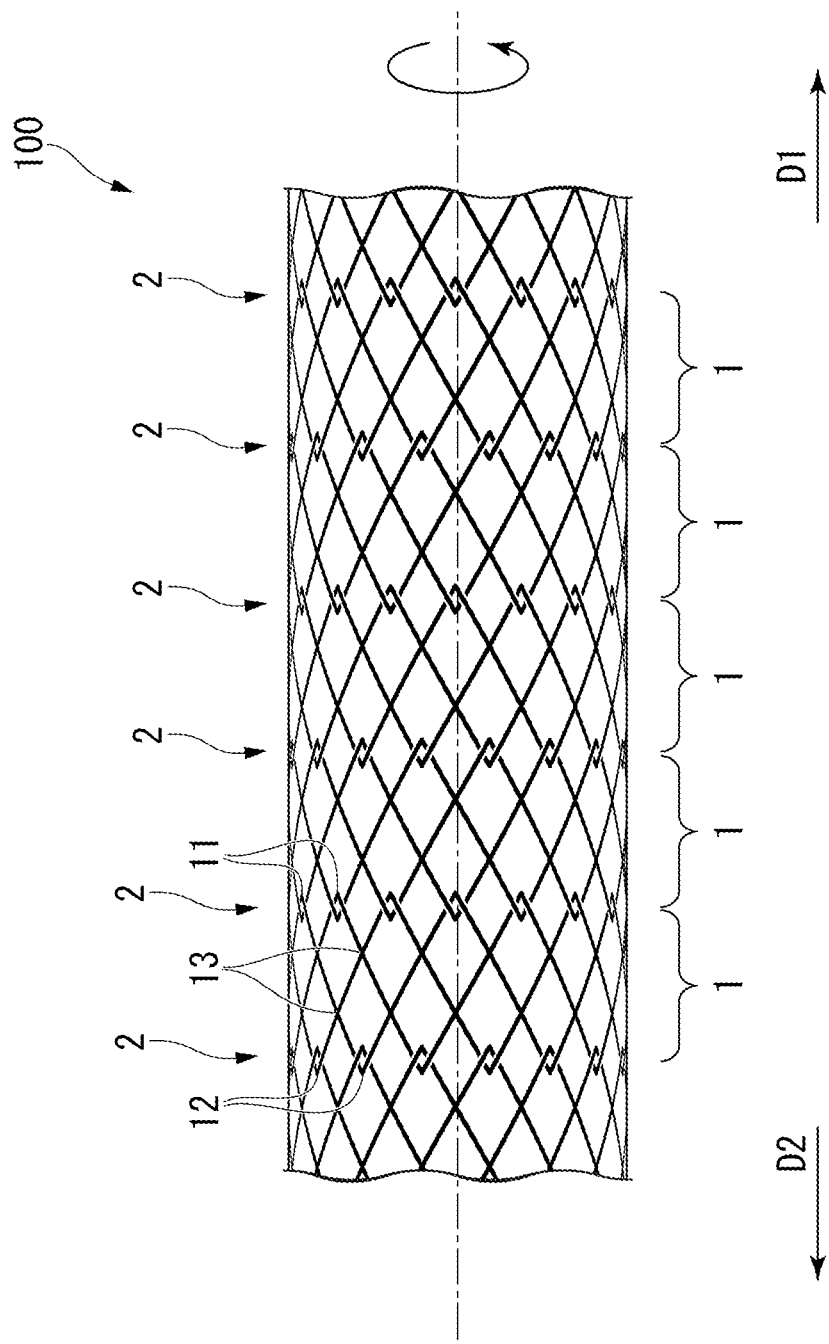
FIG. 1 is a diagram showing an overall configuration of a stent according to a first embodiment.
Figure 2:
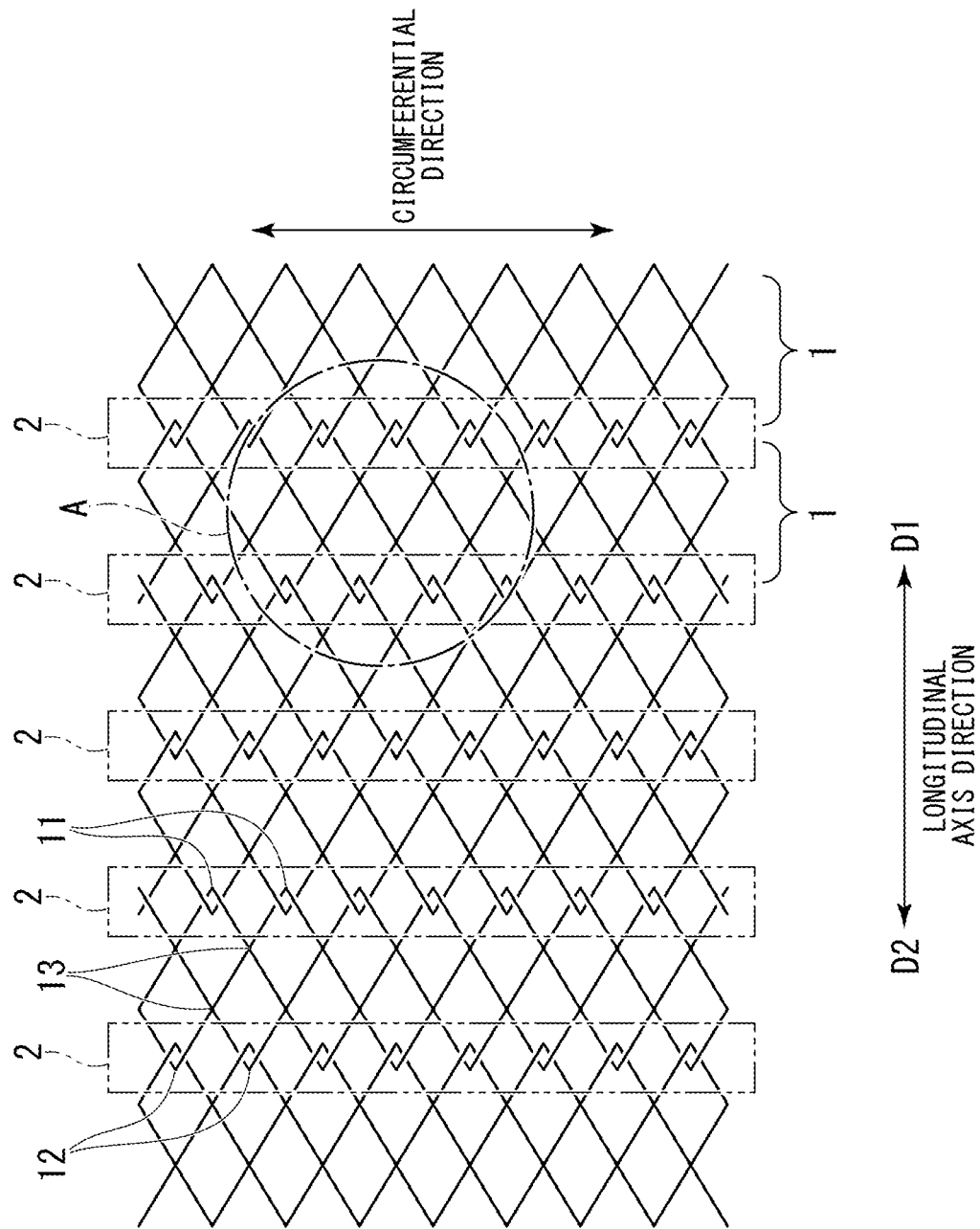
FIG. 2 is a developed view of the stent which is developed in a circumferential direction.

FIG. 1 is a diagram showing an overall configuration of a stent 100 according to the present embodiment. FIG. 1 shows an overall configuration of the stent 100 in a state of being self-expanded. FIG. 2 is a developed view of the stent 100 which is developed in the circumferential direction.

The stent 100 is formed by weaving wires and has a cylindrical tubular shape. The stent 100 is placed in the body lumen of alimentary system in the body, such as the bile duct, esophagus, duodenum, small intestine, and large intestine. The stent 100 is mainly used to expand and hold the lumen. The stent 100 according to the present embodiment is not a so-called covered stent in which an outer circumferential surface side thereof is coated with a resin film or the like, but an uncovered stent that is not coated with the film or the like. However, the stent 100 can also be used as a covered stent by being coated with a resin film or the like.

The stent 100 includes a plurality of tubular units 1 and a connecting portion 2, as shown in FIG. 1. The plurality of tubular units 1 are arranged in a longitudinal axis direction, and the adjacent tubular units 1 are connected by the connecting portion 2. In the following description, one side of the longitudinal axis direction of the stent 100 is referred to as a "first direction D1", and the other side of the longitudinal axis direction of the stent 100 is referred to as a "second direction D2".

The tubular unit (tubular portion) 1 is formed in a cylindrical tubular shape having a mesh on the circumferential surface by a wire repeatedly bent and obliquely extending in the circumferential direction. The tubular unit 1 includes a first bent part 11 in which the wires are bent, a second bent part 12 in which the wires are bent, and a straight crossing portion 13 in which the wires cross each other in a straight line.

The first bent part (bending portion on the first direction side) 11 is a convex portion in which the wire obliquely extending in the circumferential direction is folded and bent in the longitudinal axis direction to be convex toward a first direction D1 side, and a plurality of the first bent parts 11 are formed in an end portion of the first direction D1. The plurality of first bent parts 11 are arranged in the circumferential direction.

The second bent part (bending portion on second direction side) 12 is a convex portion in which the wire obliquely extending in the circumferential direction is folded and bent in the longitudinal axis direction to be convex toward a second direction D2 side, and a plurality of the second bent parts 12 are formed in an end portion of the second direction D2. The plurality of second bent parts 12 are arranged in the circumferential direction.

The connecting portion (first connecting portion) 2 is a portion in which the adjacent tubular units 1 are connected in the longitudinal axis direction, and the first bent part 11 of the tubular unit 1 on the second direction D2 side and the second bent part 12 of the tubular unit 1 on the first direction D1 side are formed to cross each other. In the connecting portion 2, since the first bent part 11 and the second bent part 12 cross each other in a "hook shape" in a radial direction and the longitudinal axis direction, the adjacent tubular units 1 are inseparably connected so as to be relatively movable.

Figure 3:
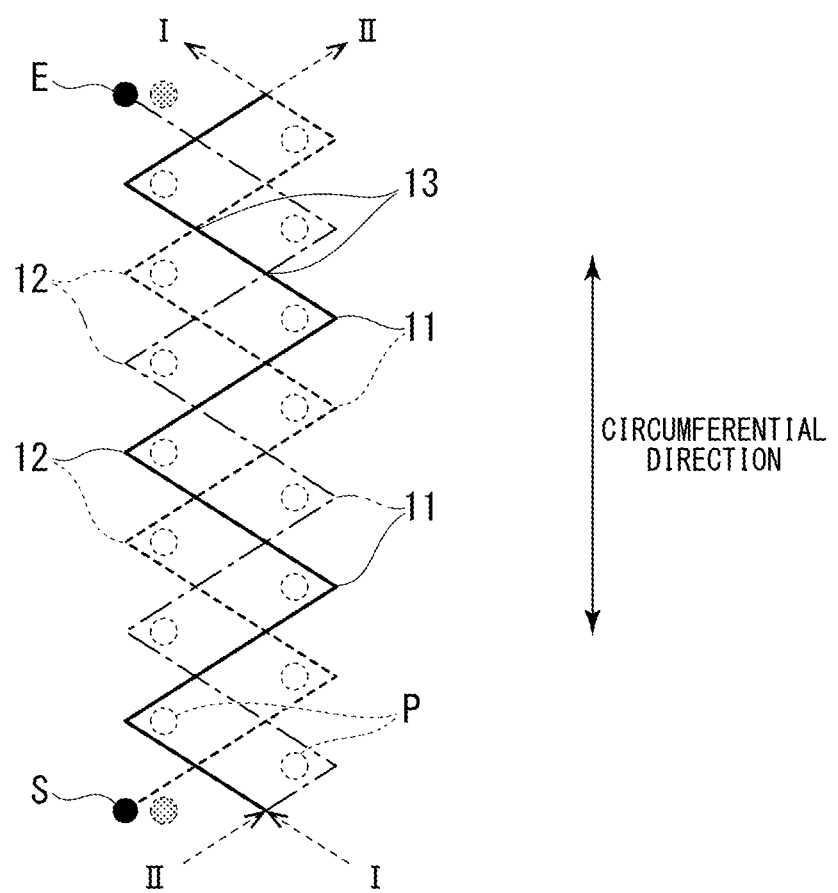
FIG. 3 is a diagram showing a weaving method of a tubular unit of the stent.

FIG. 3 is a diagram showing a weaving method of the tubular unit 1.

Figure 5:
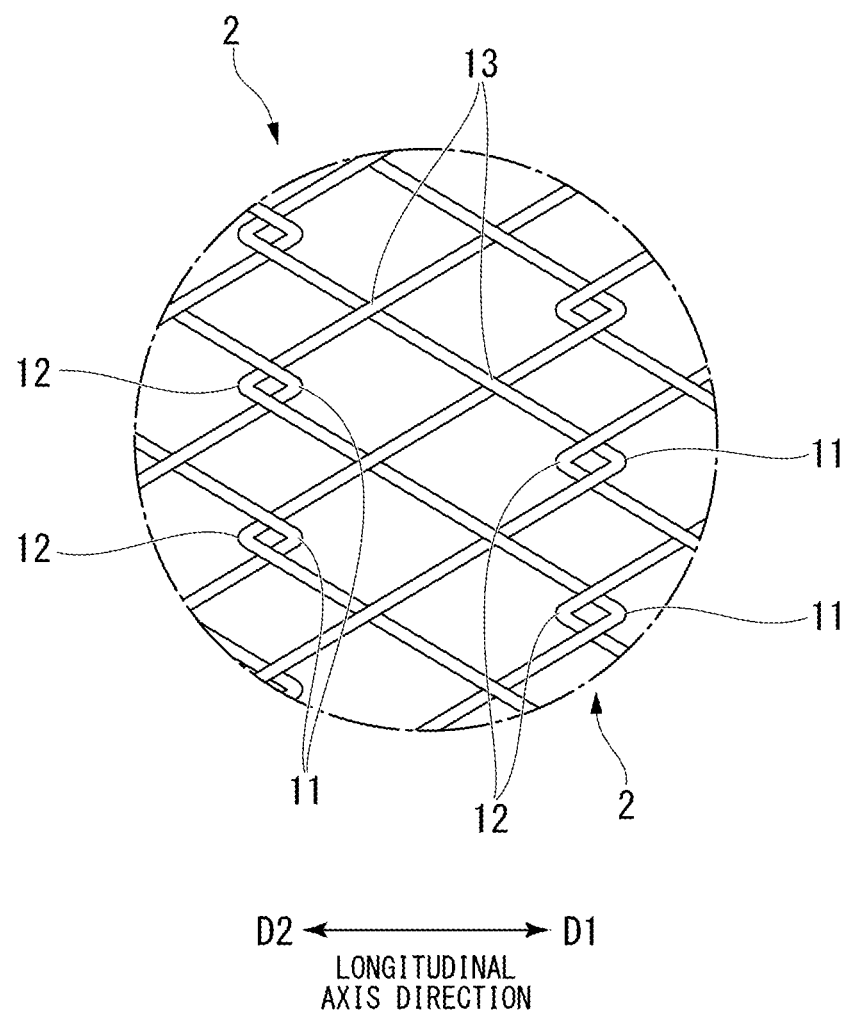
FIG. 5 is an enlarged view of a portion indicated by a dashed line in FIG. 2.

The tubular unit 1 is manufactured using a known manufacturing jig, as shown in FIG. 5 in Japanese Patent No. 3708923, for example. The manufacturing jig is formed of a cylindrical main body and a plurality of pins P erected on the outer circumferential surface of the main body. FIG. 3 is a developed view of the outer circumferential surface of the main body of the manufacturing jig in a plane. The pins P are arranged in the circumferential direction in two rows.

As shown in FIG. 3, the wires forming the tubular unit 1 obliquely extend in the circumferential direction from a start position S, and repeatedly form the first bent part 11 and the second bent part 12. The wire loops to form a first loop in the circumferential direction, and then further loops to form a second loop (portion I shown in FIG. 3).

The wire of the second loop (shown by a solid line in FIG. 3) obliquely extends in the circumferential direction, and repeatedly forms the first bent part 11 and the second bent part 12. The first bent part 11 formed by the wire of the second loop is formed between the first bent parts 11 formed by the wire of the first loop. The second bent part 12 formed by the wire of the second loop is formed between the second bent parts 12 formed by the wire of the first loop.

The wire of the second loop forms the straight crossing portion 13 crossing the wire of the first loop. The wire loops to form a second loop in the circumferential direction, and then further loops to form a third loop (portion II shown in FIG. 3).

The wire of the third loop (shown by a dashed line in FIG. 3) obliquely extends in the circumferential direction, and repeatedly forms the first bent part 11 and the second bent part 12. The first bent part 11 formed by the wire of the third loop is formed between the first bent parts 11 formed by the wire of the first loop and the first bent part 11 formed by the wire of second loop. The second bent part 12 formed by the wire of the third loop is formed between the second bent parts 12 formed by the wire of the first loop and the second bent part 12 formed by the wire of second loop.

The wire of the third loop forms the straight crossing portion 13 crossing the wire of the first loop and the wire of the second loop. The wire loops to form the third loop in the circumferential direction, and then is woven to an end point E.

Both end portions of the wire positioned at the start position S and the end point E are connected using a joining method, such as caulking, laser welding, or brazing. In FIG. 3, the wire joins the end portion of the second bent part 12, but the wire W may join the straight line portion instead of the end portion of the first bent part 11 or the second bent part 12 in consideration that stress concentration is likely to occur at the end portion.

The wire is made of a super-elastic alloy containing Nitti as a main material. The super-elastic alloy containing Nitti as the main material is not permanently deformed at the time of weaving, and the woven shape is maintained by applying heat treatment in the woven state.

The tubular unit 1 woven as described above configures two straight crossing portions 13 in a line segment of the wire connecting the first bent part 11 and the second bent part 12, as shown in FIG. 3.

Figure 4:
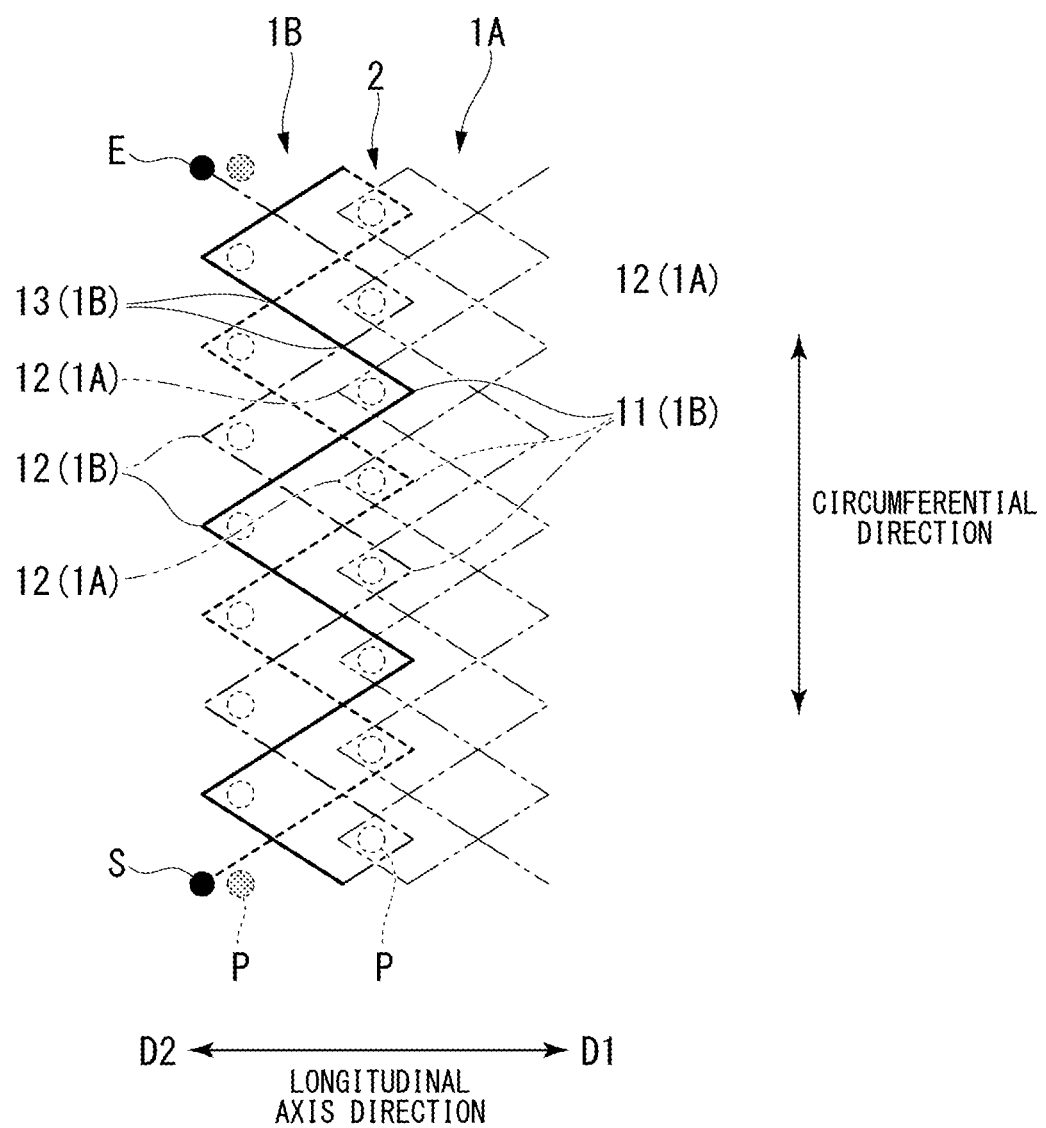
FIG. 4 is a diagram showing a weaving method of another tubular unit that is connected from a second direction side to the woven tubular unit positioned on a first direction side.

FIG. 4 is a diagram showing a weaving method of another tubular unit 1 (hereinafter, referred to as a "tubular unit 1B") connected from the second direction D2 side to the woven tubular unit 1 (hereinafter, referred to as a "tubular unit 1A") positioned on the first direction D1 side. In FIG. 4, the tubular unit 1A is indicated by a two-dot dashed line.

In a case where the tubular unit 1B is manufactured using the manufacturing jig, some of the pins are used in a case where the tubular unit 1A is shared, as shown in FIG. 4. Specifically, in FIG. 4, among the pins P arranged in the circumferential direction in two rows, the pins P arranged in one row on the first direction side are shared.

As shown in FIG. 4, the wires forming the tubular unit 1B obliquely extend in the circumferential direction from a start position S, and repeatedly form the first bent part 11 and the second bent part 12, as in the tubular unit 1A.

FIG. 5 is an enlarged view of a portion indicated by the dashed line in FIG. 2.

In a case of forming the first bent part 11, the wire forming the tubular unit 1B cross the second bent part 12 of the tubular unit 1A in a "hook shape" in the radial direction and the longitudinal axis direction to form the connecting portion 2.

As in the tubular unit 1A, the wire loops to form the third loop in the circumferential direction, and then is woven to an end point E. Both end portions of the wire positioned at the start position S and the end point E are connected using a joining method, such as caulking, laser welding, or brazing.

The tubular unit 1A and the tubular unit 1B are inseparably connected by the connecting portion 2 so as to be relatively movable. The tubular unit 1A and the tubular unit 1B is connected without adding a new connecting member.

Other tubular units 1 are connected by the connecting portion 2 by the same method as that used to connect the adjacent tubular units 1, the tubular unit 1A, and the tubular unit 1B by means of the connecting portion 2. The stent 100 is formed by connecting all of the tubular units 1.

Hereinafter, the operation of the stent 100 will be described.

The stent 100 is stored in the delivery system in a reduced diameter state and delivered to the affected area in which a stenosis or occlusion has occurred. The stent 100 released from the delivery system expands in diameter by self-expandability to expand stenosis and occlusion. The stent 100 has a simple configuration, and thus the storage diameter can be reduced in a case where the stent 100 is stored in the delivery system.

Figure 6:
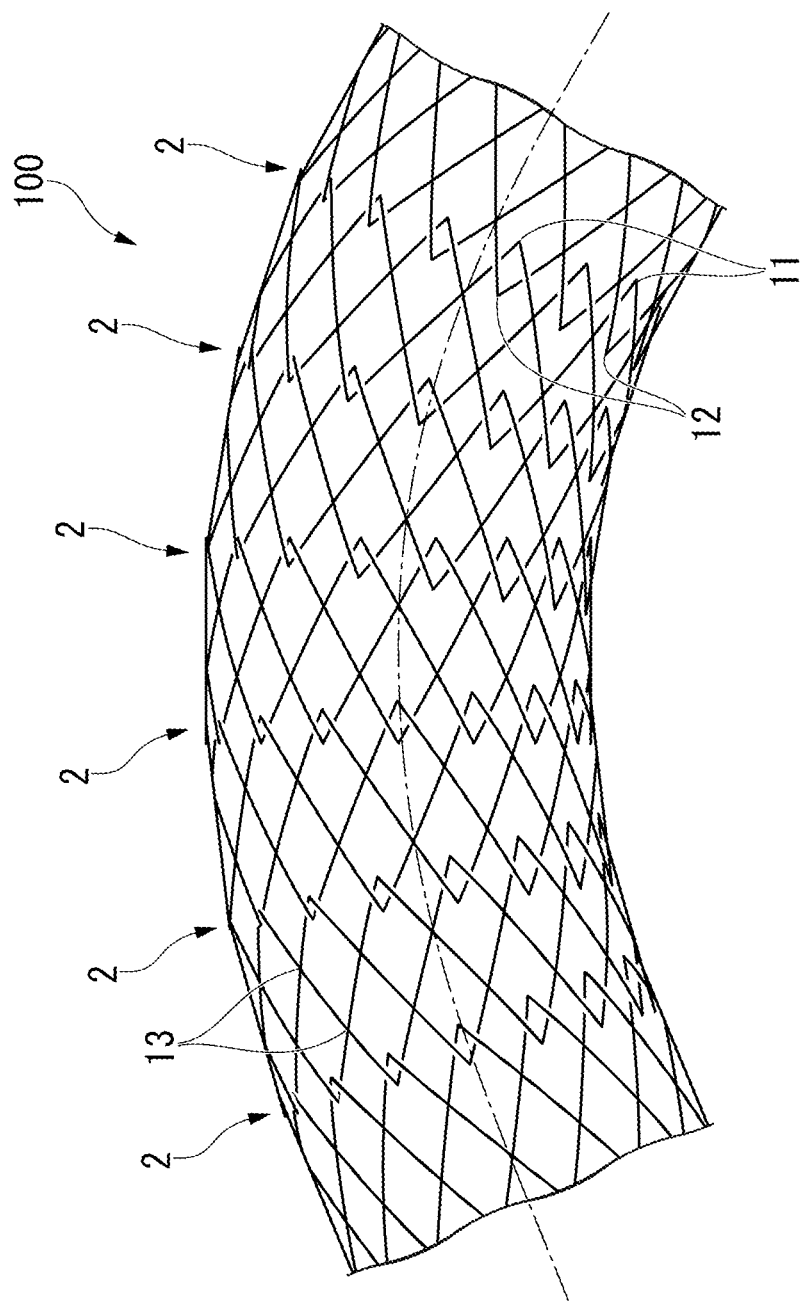
FIG. 6 shows the bending stent.

FIG. 6 shows the bending stent 100. The connecting portion 2 connects the adjacent tubular units 1 in a hook shape, and the adjacent tubular units 1 is capable of moving relatively each other. Hereinafter, the deformation of the connecting portion 2 caused due to such a movement of the adjacent tubular units 1 is referred to as "slip-deformation".

In the stent 100, in a case where the entire stent 100 is bent with respect to the longitudinal axis, as shown in FIG. 6, the connecting portion 2 arranged in the circumferential direction is "slip-deformed" and bent without "elastic deformation" of the wire that is made of super-elastic alloy. As a result, the stent 100 does not return to its original shape, and is capable of maintaining a bent shape. That is, the stent 100 has a function of maintaining a shape corresponding to the shape of the bent lumen (pipeline shape-maintaining function).

As shown in FIG. 1, in the stent 100, the connecting portions 2 are arranged in a row in the circumferential direction between the straight crossing portions 13 arranged in two rows in the circumferential direction. That is, the connecting portion 2 that can be slip-deformed and the straight crossing portion 13 that cannot be slip-deformed are disposed in the longitudinal axis direction at a ratio of 1 to 2. Therefore, the entire stent 100 is likely to be "slip-deformed", and even in a case where the lumen is significantly bent, the shape thereof corresponding to the shape of the lumen is capable of being maintained.

Figure 7:
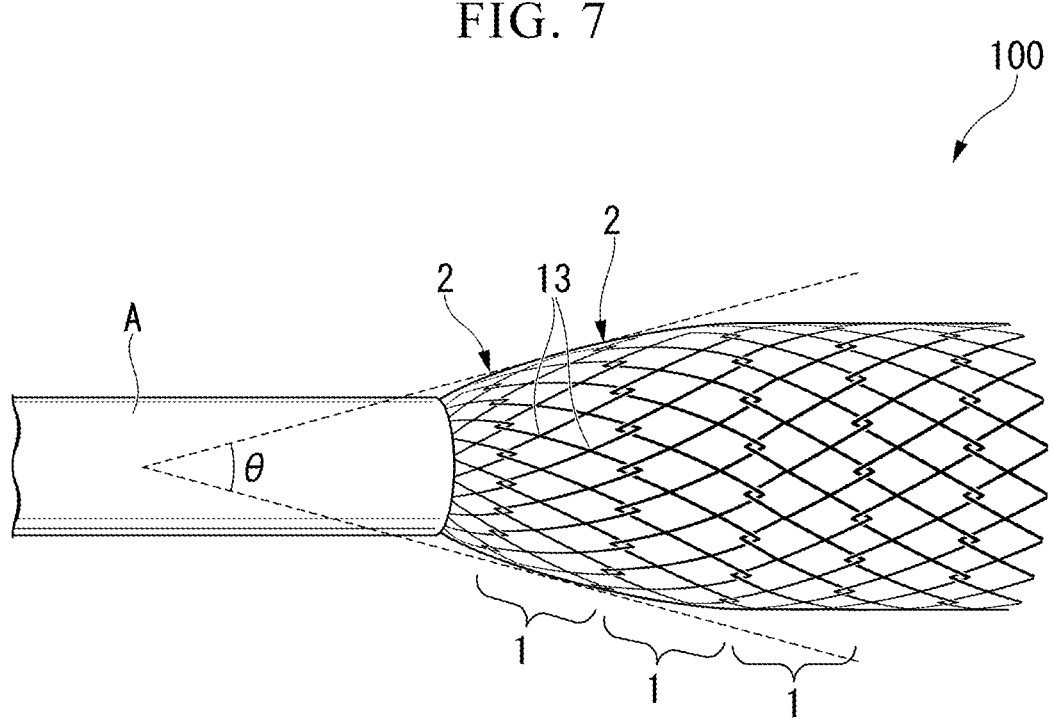
FIG. 7 shows the stent in a case of being released from a delivery system.

FIG. 7 shows the stent 100 in a case of being released from the delivery system.

In a case where the stent 100 is released from an outer sheath A at a distal end of the delivery system, since a spread angle θ of the stent 100 is capable of being reduced, the stent 100 is capable of being easily restored (recaptured) in the delivery system. That is, the stent 100 has a recapture function capable of being easily restored (recaptured) in the delivery system.

In the expansion mechanism disclosed in Japanese Patent No. 3708923, the number of "meshing portions" crossing in the hook shape is large and the spread angle of the expansion mechanism is significantly large when the expansion mechanism is released. Therefore, it is necessary to apply a large force for restoring the expansion mechanism (recaptured) in the delivery system, and making restoring (recapturing) difficult.

The stent 100 of the present embodiment has the connecting portions 2 crossing in the hook shape. Since the connecting portion 2 performs "slip-deformed", the connecting portion 2 is likely to spread in the radial direction as compared with the straight crossing portion 13 that uniformly spreads in the longitudinal axis direction, when releasing the stent 100. However, in the stent 100, the connecting portion 2 that can be slip-deformed, and the straight crossing portion 13 that cannot be slip-deformed are disposed in the longitudinal axis direction at a ratio of 1 to 2. Therefore, in a case where the stent 100 is released, the spread angle θ of the stent 100 can be reduced as compared with the expansion mechanism disclosed in Japanese Patent No. 3708923.

According to the present embodiment, the stent 100 is capable of achieving both a pipeline shape-maintaining function, and a recapture function.

As described above, the first embodiment has been described in detail with reference to the drawings. However, the specific configuration is not limited to this embodiment, and includes design changes and the like without departing from the scope of the present invention. Further, the constituent elements shown in the embodiment described above and modification examples described below can be appropriately combined and configured.

Modification Example 1

For example, in the stent 100 of the above embodiment, since the connecting portion 2 that is capable of being slip-deformed and the straight crossing portion 13 that is not slip-deformed are disposed in the longitudinal axis direction at a ratio of 1 to 2, the stent 100 is capable of achieving both the pipeline shape-maintaining function and the recapture function. However, the aspect of the stent is not limited thereto. In a case where the recapture function is further improved, in the stent, the connecting portion 2 that can be slip-deformed and the straight crossing portion 13 that cannot be slip-deformed may be disposed in the longitudinal axis direction at a ratio of 1 to 3 (or 3 or more). However, since the pipeline shape-maintaining function is suppressed as the ratio of the straight crossing portion 13 increases, it is desirable that the ratio of the straight crossing portion 13 be determined in consideration of the balance between the recapture function and the pipeline shape-maintaining function.

Second Embodiment

A second embodiment will be described with reference to FIGS. 8 and 9. In the following description, the same components as those already described will be designated by the same reference numerals and the description thereof will be omitted. A stent 100B according to the second embodiment has a different configuration to that of the connecting portion from the stent 100 according to the first embodiment.

The stent 100B includes the plurality of tubular units 1 and a connecting portion 2B. The plurality of tubular units 1 are arranged in a longitudinal axis direction, and the adjacent tubular units 1 are connected by the connecting portion 2B.

Figure 8:
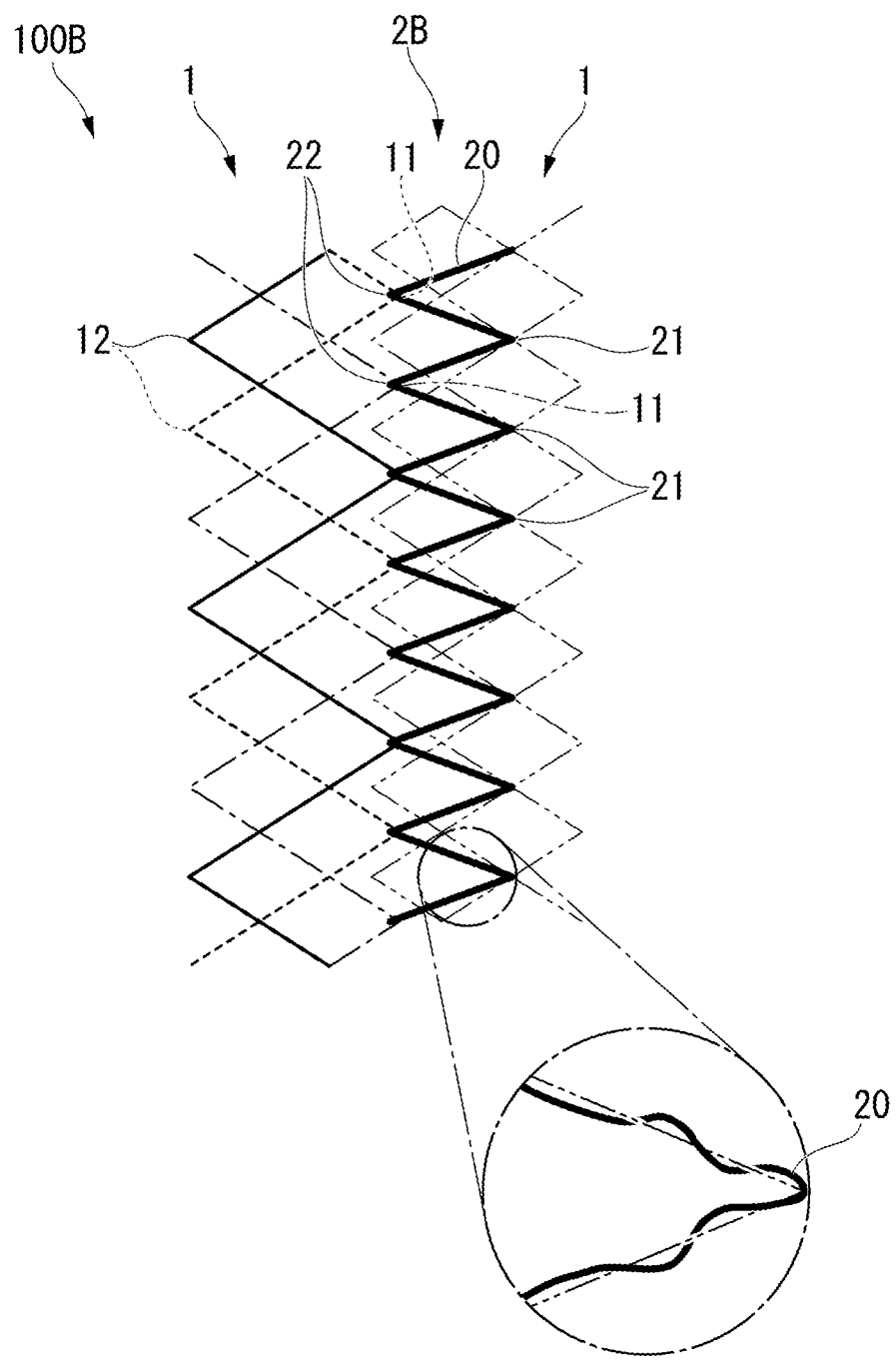
FIG. 8 is a developed view of a connecting portion of a stent according to a second embodiment which is developed in a circumferential direction.
Figure 9:
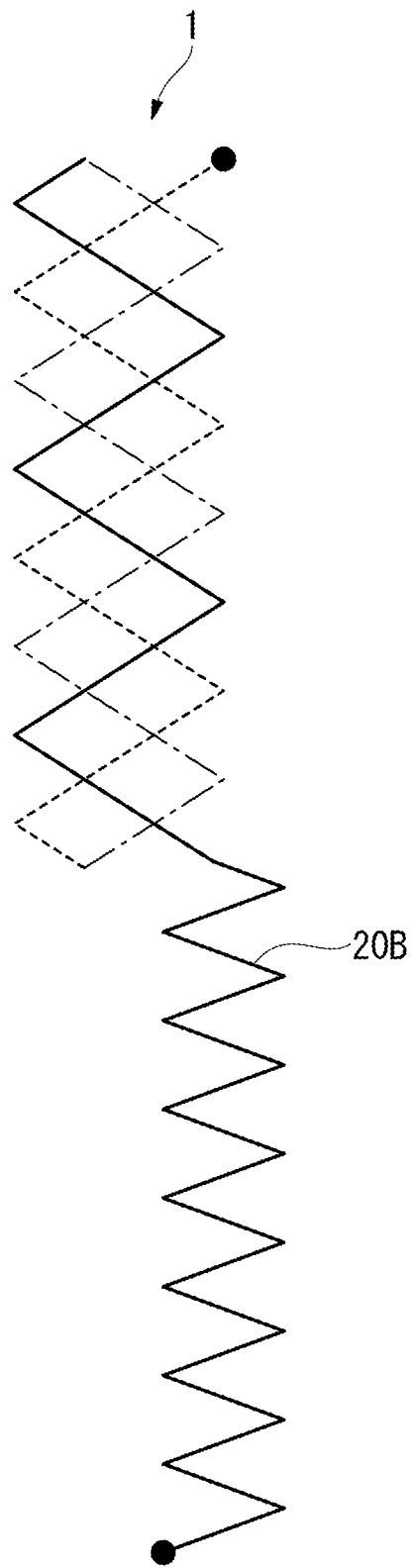
FIG. 9 is a diagram showing a modification example of a connecting wire of the stent.

FIG. 8 is a developed view of the connecting portion 2B which is developed in the circumferential direction.

The connecting portion 2B is a portion in which the adjacent tubular units 1 are connected in the longitudinal axis direction, and has a connecting wire 20.

The connecting wire 20 is repeatedly bent and obliquely extends in the circumferential direction, and forms a first bending portion 21 in which the connecting wire 20 is bent and a second bending portion 22 in which the connecting wire 20 is bent.

The first bending portion 21 of the connecting wire 20 is a convex portion in which the connecting wire 20 obliquely extending in the circumferential direction is folded and bent in the longitudinal axis direction to be convex toward a first direction D1 side. A plurality of the first bending portions 21 are formed in an end portion of the connecting wire 20 in the first direction D1. The plurality of first bending portions 21 are arranged in line in the circumferential direction.

The second bending portion 22 of the connecting wire 20 is a convex portion in which the connecting wire 20 obliquely extending in the circumferential direction is folded and bent in the longitudinal axis direction to be convex toward the second direction D2 side. A plurality of the second bending portions 22 are formed in an end portion of the connecting wire 20 in the second direction D2. The plurality of second bending portions 22 are arranged in line in the circumferential direction.

The connecting portion 2B is formed by the connecting wire 20 connecting the tubular unit 1 on the second direction D2 side and the tubular unit 1 on the first direction D1 side such that the tubular units 1 on both sides D1 and D2 are relatively movable with each other.

The first bending portion 21 of the connecting wire 20 is wound and fixed to a part of the tubular unit 1 on the first direction D1 side, as shown in FIG. 8. A fixing method and a fixing place are not limited as long as the first bending portion 21 is not separated from the tubular unit 1 on the first direction D1 side.

The second bending portion 22 of the connecting wire 20 crosses the first bent part 11 of the tubular unit 1 on the second direction D2 side. The second bending portion 22 and the first bent part 11 cross each other in a "hook shape" in the radial direction and the longitudinal axis direction.

Since the second bending portion 22 and the first bent part 11 cross each other in a "hook shape" in a radial direction and the longitudinal axis direction, the adjacent tubular units 1 connected by the connecting portion 2B are inseparably connected and are relatively movable. As a result, the first bent part 11 of the tubular unit 1 on the second direction D2 side and the second bent part 12 of the tubular unit 1 on the first direction D1 side are connected so as to be relatively movable.

Other tubular units 1 are connected to the adjacent tubular units 1 in the longitudinal direction by the connecting wire 20 of the connecting portion 2B in the same manner. The stent 100B is formed by connecting all of the tubular units 1.

According to the stent 100B of the present embodiment, both the pipeline shape-maintaining function and the recapture function capable of being restored in the delivery system is capable of being achieved, as in the stent 100 according to the first embodiment.

According to the stent 100B of the present embodiment, since the plurality of tubular units 1 are individually manufactured, and then connected by the connecting wire 20, the stent is capable of being easily manufactured.

According to the stent 100B of the present embodiment, since the connecting wire 20 has a zigzag structure (structure that obliquely extends in the circumferential direction and repeats bending) like the other wires, the diameter of the stent is capable of being easily reduced when the stent 100B is stored in the delivery system, and easily expanded when the stent 100B is released.

As described above, the second embodiment has been described in detail with reference to the drawings, but the specific configuration is not limited to this embodiment and includes design changes and the like without departing from the scope of the present invention. Further, the constituent elements shown in the above embodiments described above and the modification examples can be appropriately combined and configured.

Modification Example 2

For example, in the above embodiment, the tubular unit 1 is formed by weaving the wires, but the aspect of the tubular unit is not limited thereto. The tubular unit may be a laser cut type in which a mesh is formed on the circumferential surface of a cylindrical material by laser cutting. A plurality of tubular units may be formed by laser cutting, and then the tubular units may be connected by the connecting wire 20 to form the stent 100B.

Even in a case where the tubular unit is a laser cut type, intersection of two meshes is formed on the line connecting the first bent part 11 and the second bent part 12. In the stent 100B, the connecting portion 2 that is capable of being slip-deformed and the intersection that is not slip-deformed are disposed in the longitudinal axis direction at a ratio of 1 to 2, so that the stent 100B is capable of achieving both the pipeline shape-maintaining function and the recapture function.

Modification Example 3

For example, in the above embodiment, the connecting wire 20 is prepared separately from the tubular unit 1, but the aspect of the connecting wire is not limited thereto. FIG. 9 is a diagram showing a connecting wire 20B that is a modification example of the connecting wire 20 of the stent. The connecting wire 20B is integrally formed with the wire forming the tubular unit 1, and is used for connecting the adjacent tubular units 1 similar to the connecting wire 20. It is not necessary to prepare the connecting wire 20 separately, and the handling is easy.

Third Embodiment

A third embodiment will be described with reference to FIGS. 10 and 11. In the following description, the same components as those already described will be designated by the same reference numerals and the description thereof will be omitted. A stent 100C according to the third embodiment has a different configuration to that of the tubular unit from the stent 100 according to the first embodiment.

Figure 10:
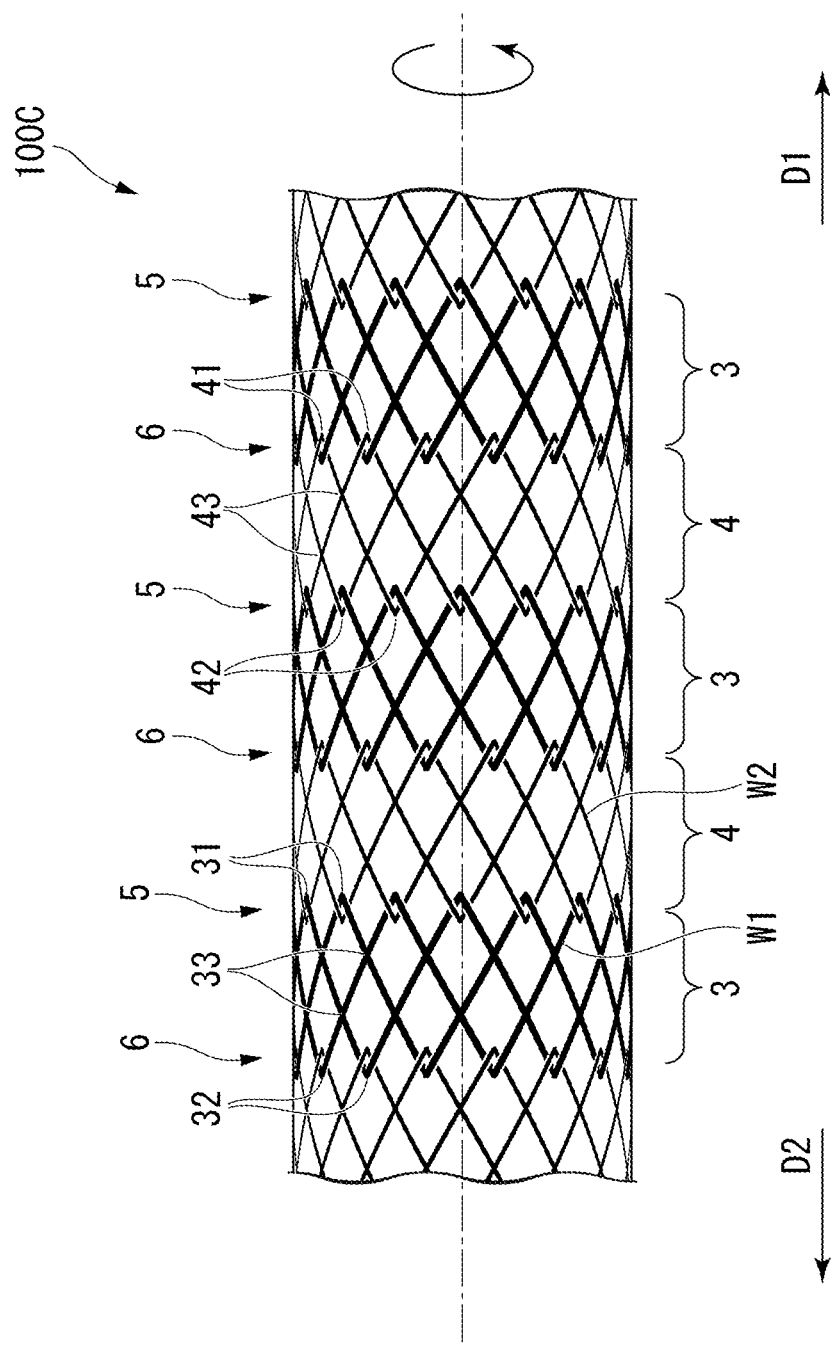
FIG. 10 is a diagram showing an overall configuration of a stent according to a third embodiment.

FIG. 10 is a diagram showing an overall configuration of a stent 100C according to the present embodiment.

The stent 100C is formed by weaving wires and has a cylindrical tubular shape as in the stent 100 according to the first embodiment.

The stent 100C includes at least one first tubular unit 3 and at least one second tubular unit 4. The first tubular unit 3 and the second tubular unit 4 are arranged alternately in the longitudinal axis direction.

The first tubular unit 3 is formed in a cylindrical tubular shape having a mesh on the circumferential surface by a wire W1 repeatedly bent and obliquely extending in the circumferential direction. The first tubular unit 3 includes a first direction bent portion 31 in which the wires W1 are bent, a first direction bent portion 32 in which the wires W1 are bent, and a first straight crossing portion 33 in which the wires W1 cross each other in a straight line.

The first direction bent portion 31 is a convex portion in which the wire W1 obliquely extending in the circumferential direction is folded and bent in the longitudinal axis direction to be convex toward the first direction D1 side, and a plurality of the first direction bent portions 31 are formed in an end portion of the first direction D1. The plurality of first direction bent portions 31 are arranged in the circumferential direction.

The first direction bent portion 32 is a convex portion in which the wire W1 obliquely extending in the circumferential direction is folded and bent in the longitudinal axis direction to be convex toward the second direction D2 side, and a plurality of the first direction bent portions 32 are formed in an end portion of the second direction D2. The plurality of first direction bent portions 32 are arranged in the circumferential direction.

The second tubular unit 4 is formed in a cylindrical tubular shape having a mesh on the circumferential surface by a wire W2 repeatedly bent and obliquely extending in the circumferential direction. The second tubular unit 4 includes a second direction bent portion 41 in which the wires W2 are bent, a second direction bent portion 42 on the second direction side in which the wires W2 are bent, and a second straight crossing portion 43 in which the wires W2 cross each other in a straight line. The second tubular unit 4 has a different shape from that of the first tubular unit 3, and in the present embodiment, the diameter dimension of the wire W1 is different from the diameter dimension of the wire W2.

The second direction bent portion 41 is a convex portion in which the wire W2 obliquely extending in the circumferential direction is folded and bent in the longitudinal axis direction to be convex toward the first direction D1 side, and a plurality of the second direction bent portions 41 are formed in an end portion of the first direction D1. The plurality of second direction bent portions 41 are arranged in the circumferential direction.

The second direction bent portion 42 is a convex portion in which the wire W2 obliquely extending in the circumferential direction is folded and bent in the longitudinal axis direction to be convex toward the second direction D2 side, and a plurality of the second direction bent portions 42 are formed in an end portion of the second direction D2. The plurality of second direction bent portions 42 are arranged in the circumferential direction.

The wire W1 which forms the first tubular unit 3 has an outer diameter of 0.17 mm to 0.18 mm On the other hand, the wire W2 which forms the second tubular unit 4 has an outer diameter of 0.15 mm, which is thinner than the wire W1. Therefore, the first tubular unit 3 has a larger expansion force to widen the stenosis radially outward as compared with the second tubular unit 4. In a case where there is inflammation or the like at the placement position of the stent 100C, the outer diameter of the wire W1 may be set to about 0.15 mm and the outer diameter of the wire W2 may be set to 0.12 mm to 0.13 mm to weaken the expansion force of the entire stent 100C. By changing the material of the wire instead of the outer diameter of the wire, the expansion force of the first tubular unit 3 may be larger than the expansion force of the second tubular unit 4.

The weaving methods of the first tubular unit 3 and the second tubular unit 4 are the same as the weaving method of the tubular unit 1 according to the first embodiment.

Figure 11:
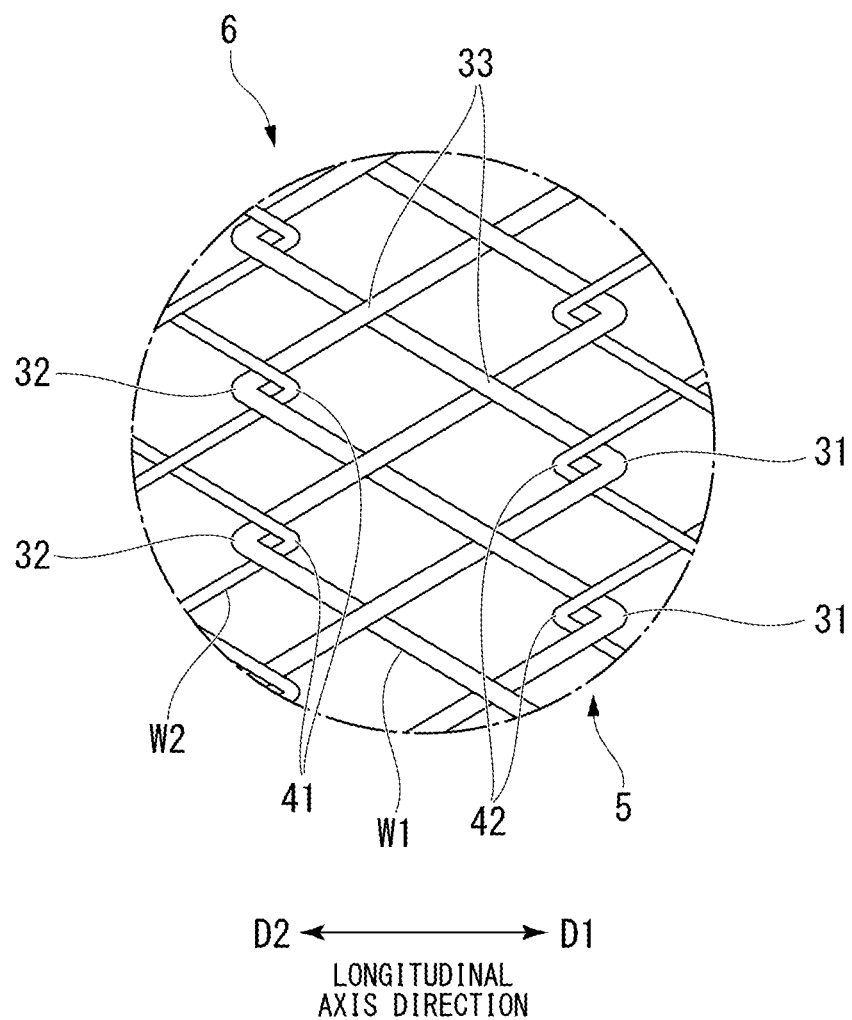
FIG. 11 is an enlarged view of a part of the stent shown in FIG. 10.

FIG. 11 is an enlarged view of a part of the stent 100C shown in FIG. 10.

The first direction bent portion 31 of the first tubular unit 3 and the second direction bent portion 42 of the second tubular unit 4 cross each other in a "hook shape" in a radial direction and the longitudinal axis direction to form a first connecting portion 5 inseparably connected so as to be relatively movable.

The direction first bent portion 32 of the first tubular unit 3 and the second direction bent portion 41 of the second tubular unit 4 cross each other in a "hook shape" in a radial direction and the longitudinal axis direction to form a second connecting portion 6 inseparably connected so as to be relatively movable.

Next, the operation of the stent 100C will be described.

The stent 100C released from the delivery system expands in diameter by self-expandability to expand stenosis and occlusion. The stent 100C includes the first connecting portion 5 and the second connecting portion 6 which are "slip-deformed" and bent as in the stent 100 according to the first embodiment, and has a function of maintaining the shape corresponding to the shape of the bent lumen (pipeline shape-maintaining function). Also, the stent 100C includes the first straight crossing portion 33 and the second straight crossing portion 43 as in the stent 100 according to the first embodiment, and has a recapture function capable of being easily restored (recaptured) in the delivery system.

With the stent 100C according to the present embodiment, the pipeline shape-maintaining function and the recapture function capable of being restored in the delivery system can be achieved at the same time.

Further, in the stent 100C, the first tubular unit 3 and the second tubular unit 4 having different expansion forces in the radial direction are alternately arranged in the longitudinal axis direction. Therefore, the outer circumferential surface of the stent 100C placed in the stenosis or the like has an uneven shape along the longitudinal axis direction. As a result, even in a case where the stent 100C is placed in a curved stenosis or the like, migration can be suitably prevented. Further, as compared with the stent having an increased total expansion force, the second tubular unit 4 having a small expansion force can be included, so that the burden on the stenosis or the like given by the entire stent 100C can be reduced, and the first tubular unit 3 having a large expansion force can be included, so that the anchor effect can be sufficiently exhibited.

As described above, the third embodiment has been described in detail with reference to the drawings, but the specific configuration is not limited to this embodiment, and includes design changes and the like without departing from the scope of the present invention. Further, the constituent elements shown in the above embodiments described above and the modification examples can be appropriately combined and configured.

Fourth Embodiment

A fourth embodiment will be described with reference to FIG. 12. In the following description, the same components as those already described will be designated by the same reference numerals and the description thereof will be omitted. A stent 100D according to the fourth embodiment has a different configuration to that of the tubular unit and the connecting portion from the stent 100C according to the third embodiment.

Figure 12:
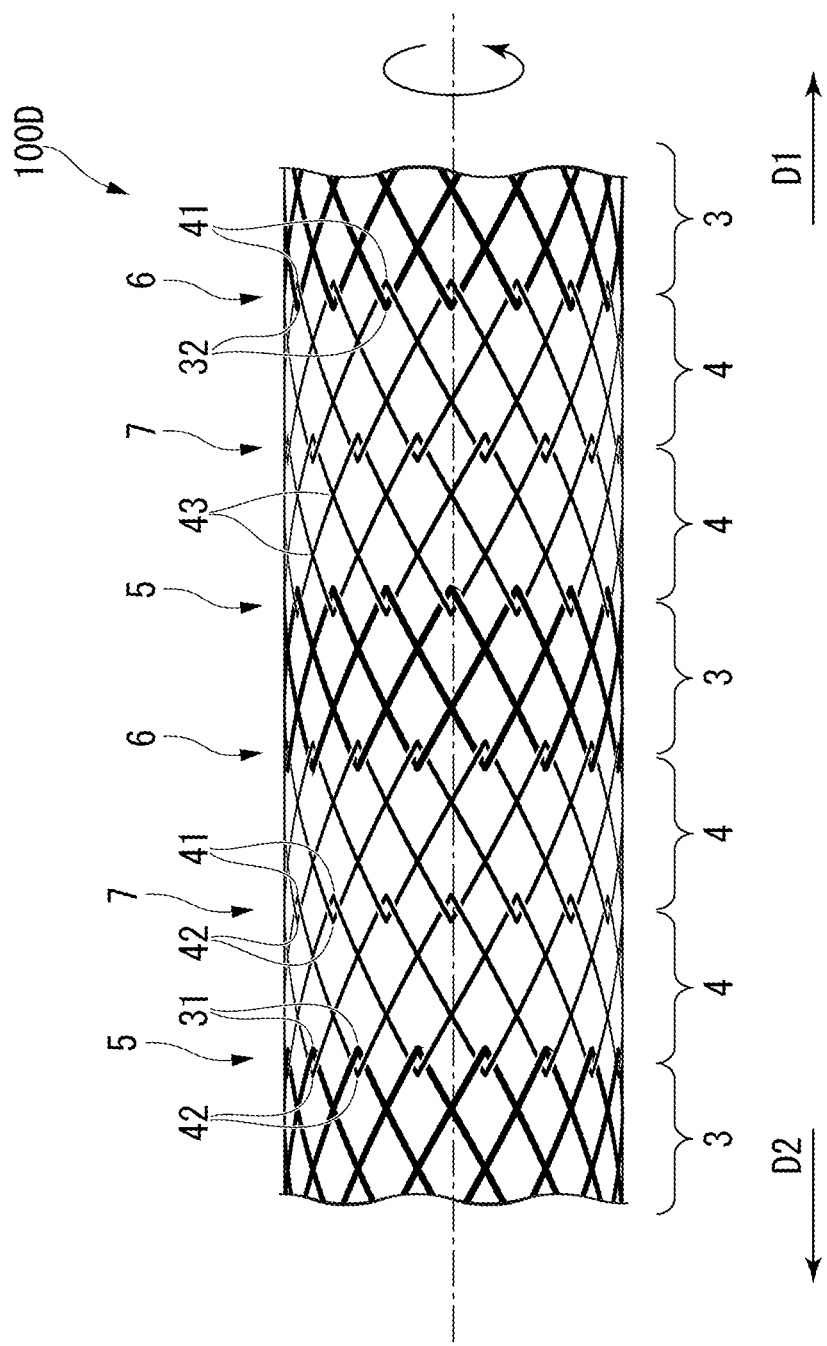
FIG. 12 is a diagram showing an overall configuration of a stent according to a fourth embodiment.

FIG. 12 is a diagram showing an overall configuration of a stent 100D according to the present embodiment.

The stent 100D is formed by weaving wires and has a cylindrical tubular shape as in the stent 100 according to the first embodiment.

The stent 100D includes at least one first tubular unit 3 and at least two second tubular units 4. The first tubular unit 3 and two adjacent second tubular units 4 are arranged alternately in the longitudinal axis direction. The first tubular unit 3 and three or more adjacent second tubular units 4 to each other may be arranged alternately in the longitudinal axis direction.

In two adjacent second tubular units 4, the second direction bent portion 42 of the second tubular unit 4 on the first direction D1 side and the second direction bent portion 41 of the second tubular unit 4 on the second direction D2 side form a third connecting portion 7 that is connected so as to be relatively movable.

In the two adjacent second tubular units 4, the second direction bent portion 41 of the second tubular unit 4 on the first direction D1 side forms the first tubular unit 3 and the second connecting portion 6.

In the two adjacent second tubular units 4, the second direction bent portion 42 of the second tubular unit 4 on the second direction D2 side forms the first tubular unit 3 and the first connecting portion 5.

With the stent 100D according to the present embodiment, the pipeline shape-maintaining function and the recapture function capable of being restored in the delivery system can be achieved at the same time, as in the stent 100C according to the third embodiment.

Further, in the stent 100D, the first tubular unit 3 and the second tubular unit 4 having different expansion forces in the radial direction are arranged in the longitudinal axis direction. Therefore, migration can be suitably prevented as in the stent 100C according to the third embodiment. Further, in the stent 100D, the number of second tubular units 4 is different from the number of first tubular units 3. Therefore, the balance between the effect of reducing the burden on stenosis and the anchor effect can be adjusted.

As described above, the fourth embodiment has been described in detail with reference to the drawings, but the specific configuration is not limited to this embodiment, and includes design changes and the like without departing from the scope of the present invention. Further, the constituent elements shown in the above embodiments described above and the modification examples can be appropriately combined and configured.

Modification Example 4

In the above embodiment, the first tubular unit 3 and the two adjacent second tubular units 4 are alternately arranged in the longitudinal axis direction, but the aspect of the combination of the tubular units is not limited thereto. The stent includes at least two first tubular units 3 and at least one second tubular unit 4, and two adjacent first tubular units 3 and the second tubular unit 4 may be alternately arranged in the longitudinal axis direction. In the two adjacent first tubular units 3, the first-second direction bent portion 32 of the first tubular unit 3 positioned on the first direction D1 side and the first first-first direction bent portion 31of the first tubular unit 3 positioned on the second direction D2 side form a fourth connecting portion 8 that is connected so as to be relatively movable. Three or more adjacent first tubular units 3 and the second tubular units 4 to each other may be arranged alternately in the longitudinal axis direction. Further, a large number of the second tubular unit 4 may be disposed at a distal end or a proximal end of the stent as compared with the first tubular unit 3. Migration can be prevented by increasing the expansion force of the distal end or the proximal end of the stent. Further, a large number of the second tubular unit 4 may be disposed at a center of the stent as compared with the first tubular unit 3. By increasing the expansion force at the center of the stent, the expandability of the stenosis part can be enhanced.

Fifth Embodiment

A fifth embodiment will be described with reference to FIG. 13. In the following description, the same components as those already described will be designated by the same reference numerals and the description thereof will be omitted. A stent 100E according to the fifth embodiment has a different configuration to that of the tubular unit from the stent 100C according to the third embodiment.

Figure 13:
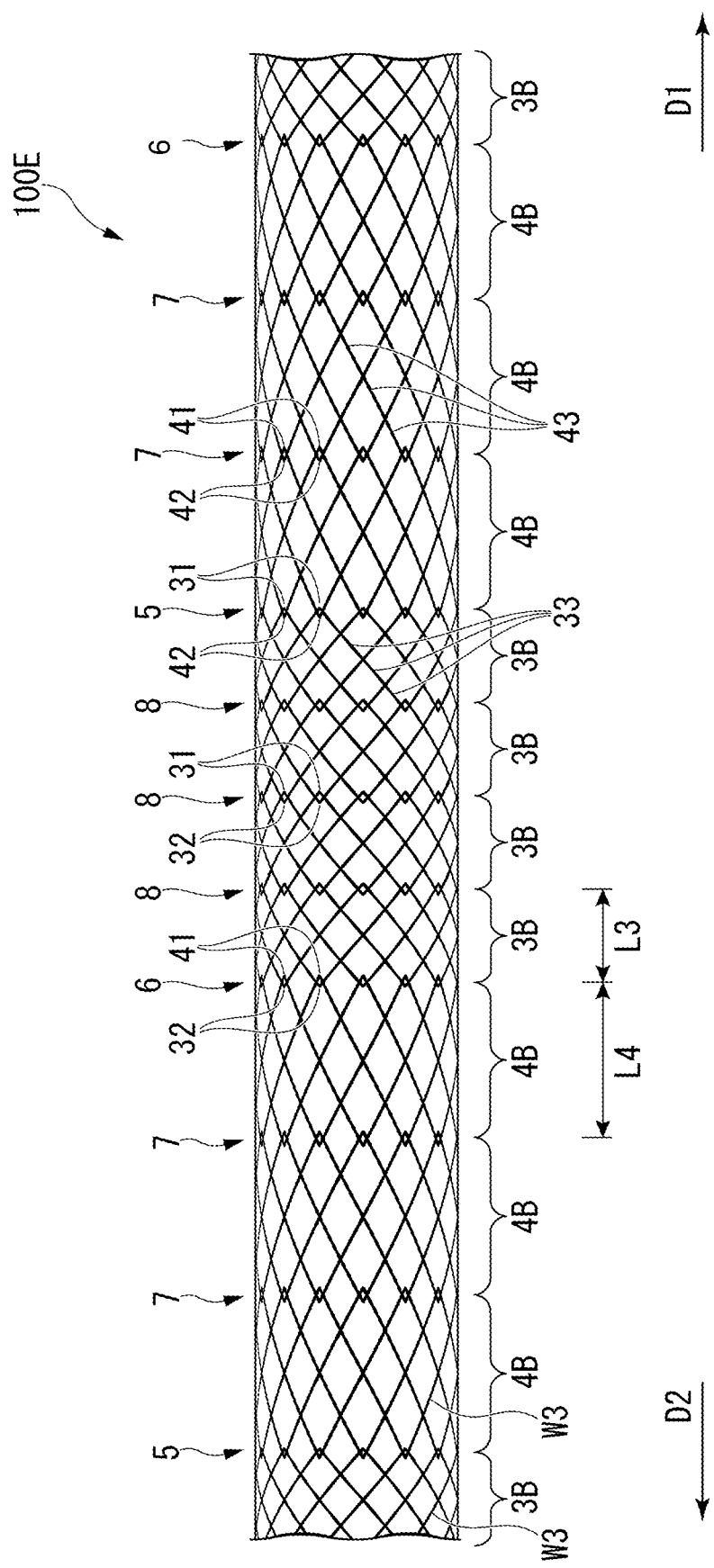
FIG. 13 is a diagram showing an overall configuration of a stent according to a fifth embodiment.

FIG. 13 is a diagram showing an overall configuration of a stent 100E according to the present embodiment.

The stent 100E is formed by weaving wires and has a cylindrical tubular shape as in the stent 100 according to the first embodiment.

The stent 100E includes at least one first tubular unit 3B and at least one second tubular unit 4B. The first tubular unit 3B and the second tubular unit 4B are arranged in the longitudinal axis direction.

The first tubular unit 3B is formed in a cylindrical tubular shape having a mesh on the circumferential surface by a wire W3 repeatedly bent and obliquely extending in the circumferential direction. The first tubular unit 3B includes a first direction bent portion 31 in which the wires W3 are bent, a first direction bent portion 32 in which the wires W3 are bent, and a first straight crossing portion 33 in which the wires W3 cross each other in a straight line.

The second tubular unit 4B is formed in a cylindrical tubular shape having a mesh on the circumferential surface by the wire W3 repeatedly bent and obliquely extending in the circumferential direction. The second tubular unit 4B includes a second direction bent portion 41 in which the wires W3 are bent, a second direction bent portion 42 in which the wires W3 are bent, and a second straight crossing portion 43 in which the wires W3 cross each other in a straight line.

The first tubular unit 3B and the second tubular unit 4B are formed by the same wire W3. The first tubular unit 3B has a different length in the longitudinal axis direction from the second tubular unit 4B. A length L3 of the first tubular unit 3B in the longitudinal axis direction is smaller than a length L4 of the second tubular unit 4B in the longitudinal axis direction. Therefore, the first tubular unit 3B has a larger expansion force to widen the stenosis radially outward as compared with the second tubular unit 4B.

The first direction bent portion 31 of the first tubular unit 3B and the second direction bent portion 42 of the second tubular unit 4B form the first connecting portion 5 inseparably connected so as to be relatively movable.

The first direction bent portion 32 of the first tubular unit 3B and the second direction bent portion 41 of the second tubular unit 4B form the second connecting portion 6 inseparably connected so as to be relatively movable.

In the two adjacent second tubular units 4B, the second direction bent portion 42 of the second tubular unit 4B on the first direction D1 side and the second direction bent portion 41 of the second tubular unit 4B on the second direction D2 side form a third connecting portion 7 that is connected so as to be relatively movable.

In the two adjacent first tubular units 3B, the first direction bent portion 32 of the first tubular unit 3B on the first direction D1 side and the first direction bent portion 31 of the first tubular unit 3B on the second direction D2 side form a fourth connecting portion 8 that is connected so as to be relatively movable.

With the stent 100E according to the present embodiment, the pipeline shape-maintaining function and the recapture function capable of being restored in the delivery system can be achieved at the same time, as in the stent 100C according to the third embodiment.

Further, in the stent 100E, the first tubular unit 3B and the second tubular unit 4B having different expansion forces in the radial direction are arranged in the longitudinal axis direction. As a result, migration can be suitably prevented as in the stent 100C according to the third embodiment.

As described above, the fifth embodiment has been described in detail with reference to the drawings, but the specific configuration is not limited to this embodiment, and includes design changes and the like without departing from the scope of the present invention. Further, the constituent elements shown in the above embodiments described above and the modification examples can be appropriately combined and configured.

Sixth Embodiment

A sixth embodiment will be described with reference to FIG. 14. In the following description, the same components as those already described will be designated by the same reference numerals and the description thereof will be omitted. A stent 100F according to the sixth embodiment has a different configuration to that the tubular unit from the stent 100C according to the third embodiment.

Figure 14:
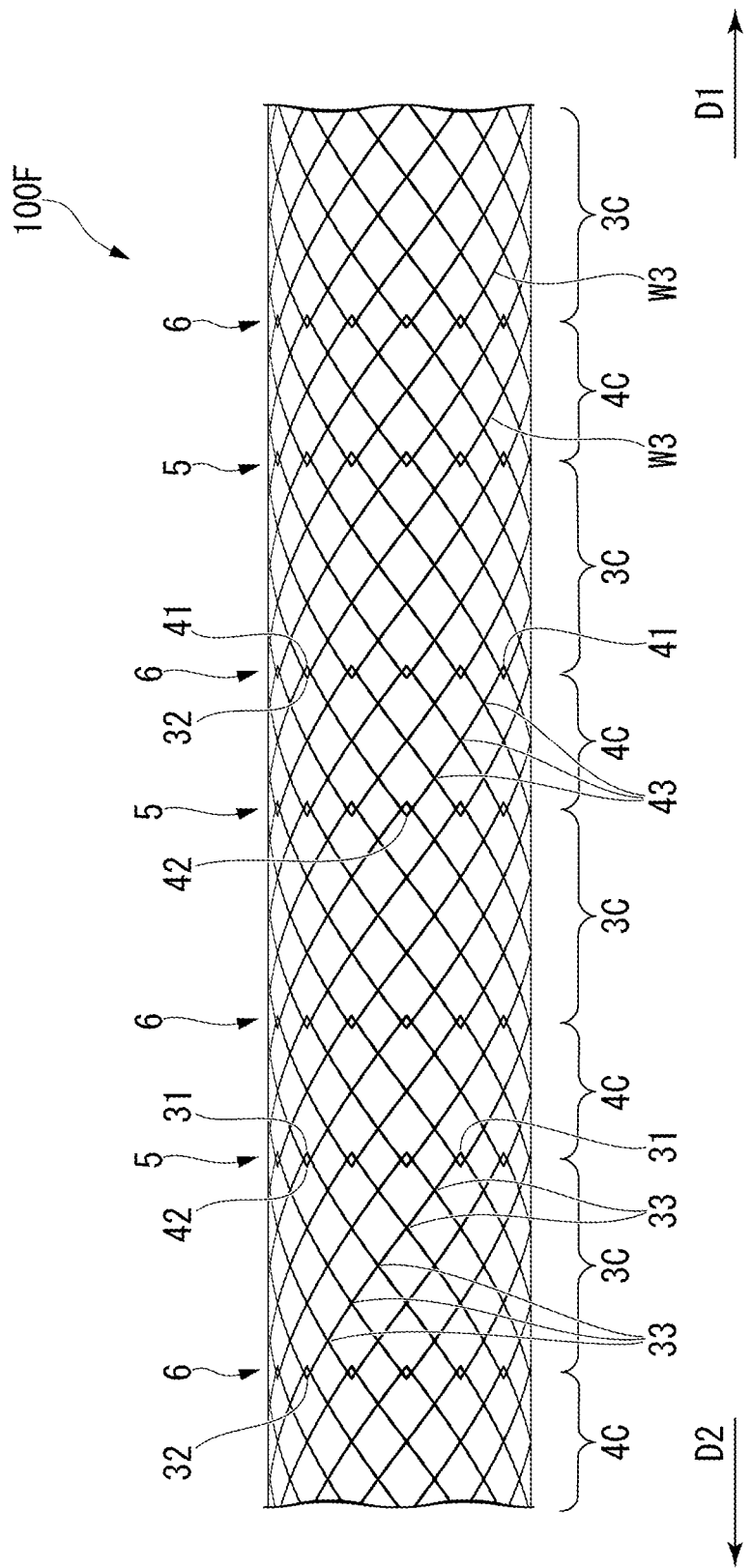
FIG. 14 is a diagram showing an overall configuration of a stent according to a sixth embodiment.

FIG. 14 is a diagram showing an overall configuration of a stent 100F according to the present embodiment.

The stent 100F is formed by weaving wires and has a cylindrical tubular shape as in the stent 100 according to the first embodiment.

The stent 100F includes at least one first tubular unit 3C and at least one second tubular unit 4C. The first tubular unit 3C and the second tubular unit 4C are arranged alternately in the longitudinal axis direction.

The first tubular unit 3C is formed in a cylindrical tubular shape having a mesh on the circumferential surface by a wire W3 repeatedly bent and obliquely extending in the circumferential direction. The first tubular unit 3C includes a first direction bent portion 31 in which the wires W3 are bent, a first direction bent portion 32 in which the wires W3 are bent, and a first straight crossing portion 33 in which the wires W3 cross each other in a straight line. The first tubular unit 3C configures five first straight crossing portions 33 in a line segment of the wire connecting the first direction bent portion 31 and the first direction bent portion 32, as shown in FIG. 14.

The second tubular unit 4C is formed in a cylindrical tubular shape having a mesh on the circumferential surface by the wire W3 repeatedly bent and obliquely extending in the circumferential direction. The second tubular unit 4C includes a second direction bent portion 41 in which the wires W3 are bent, a second direction bent portion 42 in which the wires W3 are bent, and a second straight crossing portion 43 in which the wires W3 cross each other in a straight line. The second tubular unit 4C configures three second straight crossing portions 43 in a line segment of the wire connecting the second direction bent portion 41 and the second direction bent portion 42, as shown in FIG. 14.

The number (five) of the first straight crossing portions 33 formed on a line segment of the wire W3 connecting the first direction bent portion 31 of the first tubular unit 3C to the first direction bent portion 32 is larger than the number (three) of the second straight crossing portions 43 formed on a line segment of the wire W3 connecting the second direction bent portion 41 to the second direction bent portion 42 of the second tubular unit 4C. Therefore, the first tubular unit 3C has a larger expansion force to widen the stenosis radially outward as compared with the second tubular unit 4C.

The first direction bent portion 31 of the first tubular unit 3C and the second direction bent portion 42 of the second tubular unit 4C form the first connecting portion 5 inseparably connected so as to be relatively movable.

The first direction bent portion 32 of the first tubular unit 3C and the second direction bent portion 41 of the second tubular unit 4C form the second connecting portion 6 inseparably connected so as to be relatively movable.

With the stent 100F according to the present embodiment, the pipeline shape-maintaining function and the recapture function capable of being restored in the delivery system can be achieved at the same time, as in the stent 100C according to the third embodiment.

Further, in the stent 100F, the first tubular unit 3C and the second tubular unit 4C having different expansion forces in the radial direction are arranged in the longitudinal axis direction. As a result, migration can be suitably prevented as in the stent 100C according to the third embodiment.

As described above, the sixth embodiment has been described in detail with reference to the drawings, but the specific configuration is not limited to this embodiment, and includes design changes and the like without departing from the scope of the present invention. Further, the constituent elements shown in the above embodiments described above and the modification examples can be appropriately combined and configured.

Modification Example 5

In the above embodiment, the first tubular unit 3 and the second tubular units 4 are arranged in the longitudinal axis direction, but the aspect of the stent is not limited thereto. The stent may be formed by connecting three or more tubular units by connecting portions.

What is claimed is:

1. A stent that expands a lumen of a living body, the stent comprising:
   a tubular body having a cylindrical tubular shape, a first end and a second end opposite to the first end, the tubular body comprising:
      a first tubular body portion having one or more of first wires defining a first mesh circumferential surface; and
      a second tubular body portion having one or more of second wires defining a second mesh circumferential surface the second tubular body portion being connected to the first tubular body portion in a longitudinal axis direction of the tubular body,
   wherein one or more of first wires are different from one or more of second wires,
   the first tubular body portion has first bent portions and second bent portions, the first bent portions being bent to be convex relative to a first direction toward the first end, the second bent portions being bent to be convex relative to a second direction toward the second end,
   the second tubular body portion has third bent portions and fourth bent portions, the third bent portions being bent to be convex relative to the first direction, the fourth bent portions being bent to be convex relative to the second direction,
   the first bent portions and the fourth bent portions are linked together at a first connecting portion, the first bent portions and the fourth bent portions being connected so as to be movable relative to each other;
   the first tubular body portion includes a plurality of first straight crossing portions, the plurality of first straight crossing portions intersecting each other at the first mesh circumferential surface without linking together; and
   the second tubular body portion includes a plurality of second straight crossing portions, the plurality of second straight crossing portions intersecting each other at the second mesh circumferential surface without linking together.

2. The stent according to claim 1, wherein the second tubular body portion has a second longitudinal length different from a first longitudinal length of the first tubular body portion.

3. The stent according to claim 2, wherein
the second bent portions of the first tubular body portion and the third bent portions of the second tubular body portion are linked together at a second connecting portion, the second bent portions and the third bent portions being connected so as to be movable relative to each other.

4. The stent according to claim 3,
wherein the second tubular body portion comprises two or more second tubular body portions adjacent to each other in the longitudinal axis direction, and
the fourth bent portions of a first of the two or more second tubular body portions at a first direction side of the tubular body and the third bent portions of a second of the two or more second tubular body portions at a second direction side of the tubular body are linked together at a third connecting portion, the third bent portions and the fourth bent portions being connected so as to be movable relative to each other.

5. The stent according to claim 4,
wherein the two or more second tubular body portions are disposed adjacent to each other at one of a distal end, a proximal end, or a center of the tubular body.

6. The stent according to claim 3,
wherein the first tubular body portion comprises two or more first tubular body portions adjacent to each other in the longitudinal axis direction, and
the second bent portions of a first of the two or more first tubular body portions at a first direction side of the tubular body and the first bent portions of a second of the two or more first tubular body portions at a second direction side of the tubular body are linked together at a fourth connecting portion, the first bent portions and the second bent portions being connected so as to be movable relative to each other.

7. The stent according to claim 3, wherein the first tubular body portion and the second tubular body portion are alternately arranged in the longitudinal axis direction.

8. The stent according to claim 1,
wherein a first diameter of the one or more first wires is greater than a second diameter of the one or more second wires.

9. The stent according to claim 1, wherein a number of the plurality of second straight crossing portions is larger than a number of the plurality of first straight crossing portions, the number of the plurality of first straight crossing portions are on a first segment of the one or more first wires between a corresponding first bent portion and a corresponding second bent portion, the number of the plurality of second straight crossing portions are on a second segment of the one or more second wires between a corresponding third bent portion and a corresponding fourth bent portion.

10. The stent according to claim 1,
wherein the first tubular body portion is formed by crossing and weaving one or more first wires and the second tubular body portion is each formed by crossing and weaving one or more second wires,
wherein the plurality of first straight crossing portions comprise the one or more first wires crossing each other in a straight line, and the plurality of second straight crossing portions comprise the one or more second wires crossing each other in a straight line.

11. The stent according to claim 1, further comprising a connecting wire wound around at least one of the first bent protions of the first tubular body portion and hooking a corresponding fourth bent portion of the second tubular body portion at the first connecting portion to connect the first tubular body portion and the second tubular body portion.

12. A stent comprising:
a tubular body having a cylindrical tubular shape, a first end and a second end opposite to the first end, the tubular body comprising:
a first tubular body portion comprising a plurality of first wires;
a second tubular body portion comprising a plurality of second wires;
the first tubular body portion has first bent portions and second bent portions, the first bent portions being bent to be convex relative to a first direction toward the first end, the second bent portions being bent to be convex relative to a second direction toward the second end;
the second tubular body portion has third bent portions and fourth bent portions, the third bent portions being bent to be convex relative to the first direction, the fourth bent portions being bent to be convex relative to the second direction; and
the first bent portions and the fourth bent portions are linked together at a first connecting portion so as to be relatively movable;
the first tubular body portion includes a plurality of first straight crossing portions, the plurality of first straight crossing portions intersecting each other without linking together; and
the second tubular body portion includes a plurality of second straight crossing portions, the plurality of second straight crossing portions intersecting each other without linking together; and
a number of the plurality of first straight crossing portions is larger than a number of the plurality of second straight crossing portions, the number of the plurality of first straight crossing portions are on a first segment of each individual first wire of the plurality of first wires between a corresponding first bent portion and a corresponding second bent portion, the number of the plurality of second straight crossing portions are on a second segment of each individual second wire of the plurality of second wires between a corresponding third bent portion and a corresponding fourth bent portion.

13. The stent according to claim 12, wherein the plurality of first wires form a first mesh circumferential surface and the plurality of second wires form a second mesh circumferential surface.

14. The stent according to claim 12, wherein:
the second bent portions of the first tubular body portion and the third bent portions of the second tubular body portion are linked together at a second connecting portion, the second bent portions and the third bent portions being connected so as to be movable relative to each other.

15. A stent that expands a lumen of a living body, the stent comprising:
a tubular body having a cylindrical tubular shape, a first end and a second end opposite to the first end, the tubular body comprising:

a first tubular body portion comprising one or more first wires forming a first mesh circumferential surface; and a second tubular body portion comprising one or more second wires forming a second mesh circumferential surface, the second tubular body portion being connected to the first tubular body portion in a longitudinal axis direction of the tubular body, wherein the first tubular body portion has first bent portions and second bent portions, the first bent portions being bent to be convex relative to a first direction toward the first end, the second bent portions being bent to be convex relative to a second direction toward the second end, the second tubular body portion has third bent portions and fourth bent portions, the third bent portions being bent to be convex relative to the first direction, the fourth bent portions being bent to be convex relative to the second direction, the first bent portions and the fourth bent portions are linked together at a first connecting portion;

the first tubular body portion includes a plurality of first straight crossing portions, the plurality of first straight crossing portions intersecting each other at the first mesh circumferential surface without linking together;

the second tubular body portion includes a plurality of second straight crossing portions, the plurality of second straight crossing portions intersecting each other at the second mesh circumferential surface without linking together; and a number of the plurality of first straight crossing portions is larger than a number of the plurality of second straight crossing portions, the number of the plurality of first straight crossing portions are on a first segment of each individual first wire of the plurality of first wires between a corresponding first bent portion and a corresponding second bent portion, the number of the plurality of second straight crossing portions are on a second segment of each individual second wire of the plurality of second wires between a corresponding third bent portion and a corresponding fourth bent portion.

16. The stent according to claim 15, wherein the first bent portions and the fourth bent portions being connected so as to be movable relative to each other.

17. The stent according to claim 15, further comprising a connecting wire wound around at least one of the first bent portions of the first tubular body portion and the hooking a corresponding fourth bent portion of second tubular body portion at the first connecting portion to connect the first tubular body portion and the second tubular body portion.

* * * * *